United States Patent [19]

Chang

[11] Patent Number: 5,250,021
[45] Date of Patent: Oct. 5, 1993

[54] FOOT AND ANKLE BRACE

[76] Inventor: Shin-Ju D. Chang, P.O. Box 1383, South Pasadena, Calif. 91301

[21] Appl. No.: 832,913

[22] Filed: Feb. 10, 1992

[51] Int. Cl.$^5$ .............................................. A61F 5/00
[52] U.S. Cl. ........................................ 602/27; 602/23
[58] Field of Search ............ 602/5, 10, 11, 23, 27–29; 36/110, 35 B, 15, 101, 3 B, 29

[56] References Cited

U.S. PATENT DOCUMENTS

| | | | |
|---|---|---|---|
| 3,902,259 | 9/1975 | Cracco | 36/101 X |
| 3,999,540 | 12/1976 | Freeman | 602/10 X |
| 4,005,704 | 2/1977 | Stohr et al. | 602/11 |
| 4,144,659 | 3/1979 | Eisenberg | 482/79 X |
| 4,262,433 | 4/1981 | Hagg et al. | 36/35 B X |
| 4,462,171 | 7/1984 | Whispell | 36/3 B |
| 4,570,363 | 2/1986 | Annovi | 36/15 X |
| 4,572,169 | 2/1986 | Mauldin et al. | 602/27 |
| 4,771,768 | 9/1988 | Crispin | 602/27 X |
| 4,887,369 | 12/1989 | Bailey et al. | 36/15 X |
| 4,962,760 | 10/1990 | Jones | 602/27 |
| 4,974,583 | 12/1990 | Freitas | 602/27 X |
| 5,078,128 | 1/1992 | Grim et al. | 602/23 |
| 5,092,321 | 3/1992 | Spademan | 602/27 |

FOREIGN PATENT DOCUMENTS 2032761  5/1980  United Kingdom ............... 36/35 B Primary Examiner—Richard J. Apley
Assistant Examiner—Linda C. M. Dvorak
Attorney, Agent, or Firm—Ladas & Parry

[57] ABSTRACT

An ankle brace comprising a shoe base for releasable attachment to the foot of a patient, the base including lateral sides, a sole support, a toe end, and a heel end, the ankle brace further comprising leg supports for rigid attachment to the shoe base and adapted to be strapped to the leg of a patient above the patient's ankle. Attachment means are provided for attaching the leg supports to the shoe base, for securing the leg supports to the sides of the base, and for resisting twisting and rotational torques applied to the leg supports relative to the shoe base. In one embodiment, such torques are resisted by interacting vertical members on the shoe base and leg supports. In another embodiment, the leg supports are secured to the sole support inwardly of the side of the base. An air cushion for the heel portion of the shoe base may be provided to absorb impactive forces when the patient is walking. The main body of the shoe base is formed with a smooth sole support on its top surface and a plurality of open adjacent cellular cavities on its bottom. The cavities have closed walls on their tops and sides and are open at their lower extremities. The bottom sole is adapted to fit over and close off the open cavities.

17 Claims, 1 Drawing Sheet

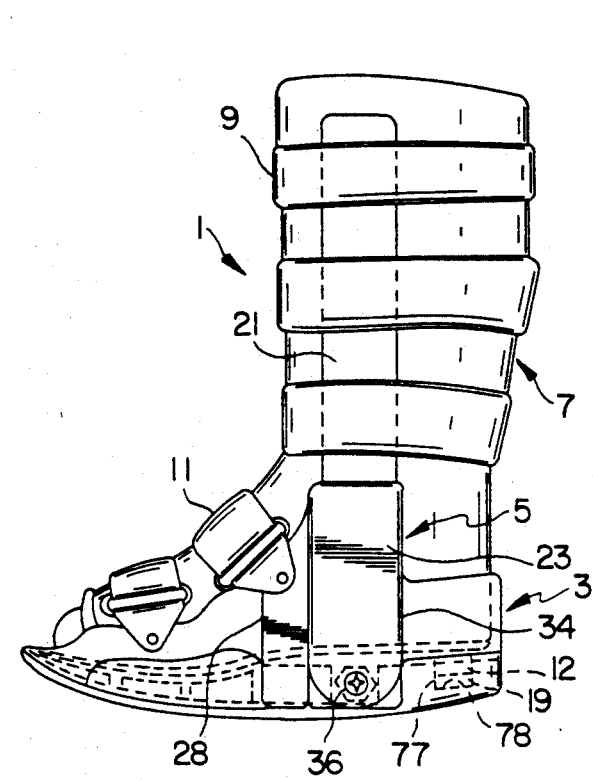
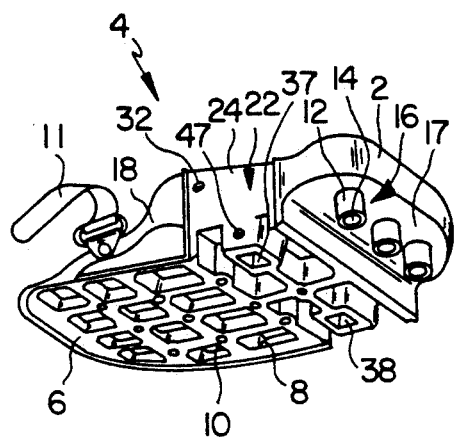
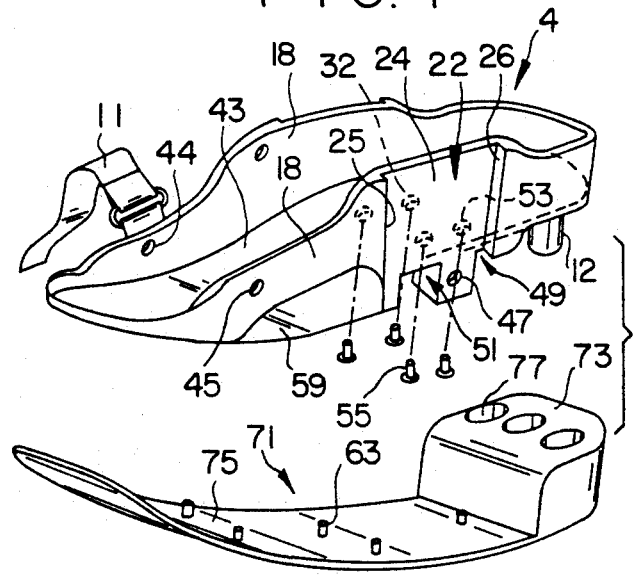
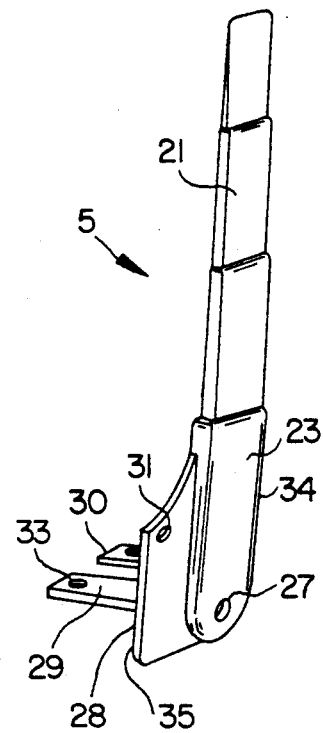

FOOT AND ANKLE BRACE

BACKGROUND OF THE INVENTION

1. Field of the Invention

This invention relates to the field of foot and ankle braces, and in particular to a foot and ankle brace which provides high strength, torsion resistance, a top sole support formed integrally as part of a one-piece shoe base main body, improved shock absorbing characteristics, a locking mechanism between the vertical uprights for the brace and the sides of the shoe base, and lightweight construction.

2. Description of the Prior Art

A number of orthotic braces, often referred to as "walkers" have been developed for aid in the rehabilitation of ankle fractures. The object of such braces is to immobilize the ankle and yet permit weight bearing and walking of the patient. Such braces are often used after an initial period of time in which the ankle is immobilized in a rigid cast. This invention relates to those ankle braces which permit the patient to walk with the brace in place.

While prior art walkers have provided many advantages to the patient when compared with a rigid cast, they also have disadvantages which have caused discomfort and anxiety in a patient. For example, the hard material from which the base or shoe portion of the brace is made imparts a substantial shock to the patient's foot and ankle for each step he or she takes. Furthermore, such prior art ankle braces, while providing a fixed vertical upright brace which can be bound to the leg of the patient below the knee, there is a tendency to deform the ankle brace by the constant application of rotational torque between the vertical upright and the shoe base portion. When the torque applied between the vertical uprights and the shoe base is sufficient to upset the initially prescribed angle between the two elements, the uprights become loose or are twisted, so that the ankle is maintained at an improper relationship relative to the leg. Walking in such distorted position can be painful, and cause obvious extreme difficulties if not discovered early and replaced with a new brace. Finally, prior art shoe bases have been constructed of several complex pieces making construction and stocking of different shoe sizes very expensive.

Some attempts have been made to overcome the deficiencies noted above. However, such attempts have been inadequate. For example, in U.S. Pat. No. 4,771,768, a rocker for the ankle brace is made from a high impact rigid plastic material with the top of the interior surface thereof being formed by the top edges of spaced apart and parallel longitudinal ribs integral with perpendicular spaced apart parallel lateral ribs molded into the inside bottom portion of the rocker. While such construction serves to reduce the weight of the shoe portion, it is complicated by the fact that two major structural portions of the shoe base must be molded in order to produce a composite shoe base. According to U.S. Pat. No. 4,771,768, the base portion is provided with upstanding ribs which support the undersurface of a foot pad. If molded, the interior surface upon which the foot pad rests is formed by the top edges of spaced apart and longitudinal ribs integral with spaced apart parallel lateral ribs. In other words, the foot pad is necessarily rather thick because it sits upon a matrix of rib edges and would otherwise cause discomfort to the wearer, because the tops of the ribs would impress upon the bottom of the wearer's foot. In the upper portion of this prior art device, means are provided for attaching straps, and for receiving the lower end of the vertical uprights. The bottom portion of the shoe base includes the bottom sole and the complex arrangement of upstanding ribs on the upper surface of the bottom sole plate. As a result, the shoe base of this prior art ankle brace necessarily requires the manufacturing and later assembling of two separate complex parts. Also, since the inner sole upon which the foot rests is not formed as part of the ribbed support construction, an exceptionally thick foot pad is required. Finally, in the molded version of the shoe base, any twisting torque applied to the shoe base from the uprights must be absorbed primarily by the bottom surface of the open top cellular shell. This means that, due to the length of the uprights, severe stress is applied to and resisted by the bottom surface of the shell. As a result, the bottom surface could buckle, or the connection between the upright and the shoe could develop fractures leading ultimately to breakage.

The shoe of U.S. Pat. No. 4,974,583 suffers from the same deficiencies as those discussed in connection with U.S. Pat. No. 4,771,768, inasmuch as the former also teaches the construction of the shoe to include a support surface formed by ribs whose edges support layers of plastic or plastic foam for receiving the sole of a patient's foot. Any open cellular shoe base having upstanding ribs upon which a soft foot pad is placed is subject to the same critique: 1) they offer a very uncomfortable foot support surface (being the tops of a ribbed matrix), and 2) they absorb twisting torque from the uprights basically at the floor level producing great stress at the upright/shoe base connection.

While most ankle braces appear to have a single pivotal joint joining the vertical braces with the shoe portion (e.g. U.S. Pat. No. 4,510,927), there have been some attempts to make the connection between the vertical uprights and the shoe base more resistant to torque applied forces. For example in U.S. Pat. Nos. 4,414,965 and 4,378,793, the vertical uprights are attached to the sole of the shoe portion by a number of screws passing through the bottom of the vertical uprights and into the side of the bottom sole of the shoe. Such arrangement holds the uprights snugly against the sides of the sole portion of the shoe, but falls short of resisting deformation upon the application of a large torque acting to rotate the vertical uprights relative to the plane of the shoe sole. Even a large number of screws would not prevent this from happening, since the sole is typically formed of a molded plastic material, and the screws would "give" in the sheer direction with even moderately applied torsional forces. Furthermore, when the vertical uprights are relatively thin, as they are in the latter-two-mentioned patents, the sides of the holes through which the screws pass will permit an unacceptable amount of rotation between the uprights and the shoe base due to tolerance of the hole sizes relative to the body of the screws and wear on the screws and on the interior surfaces of the holes in the bottom of the uprights.

It can generally be concluded that in all existing walkers, large torque forces or shear forces are transmitted through the bottom of the shoe which causes some deformation of the sole support at the patient's foot level.

Another problem with prior art ankle braces is the twisting off or slipping of the heel part of the sole relative to the main body of the shoe due to constant impact with the ground and the natural outturning of the shoe as the patient walks. In the past, this problem has been addressed by simply providing softer plastic material in the heel portion, but that solution is not entirely effective and gives a very unnatural feel to the shoe when walking.

Accordingly, there is a need in the art to provide an ankle brace assembly which is not subject to the deficiencies noted above. The present invention satisfies this need.

SUMMARY OF THE INVENTION

The present invention overcomes the aforementioned difficulties by providing an ankle brace comprising a shoe base for releasable attachment to the foot of a patient, the base including lateral sides, a sole plate, a toe end, and a heel end, the ankle brace further comprising leg support means for rigid attachment to the shoe base and adapted to be strapped to the leg of a patient above the patient's ankle. Attachment means are provided for attaching the leg support means to the shoe base, such attachment means including first securing means for securing the leg support means to one side of the base, and second securing means for securing the leg support means to the sole plate inwardly of the side of the base and laterally of the first securing means. In a preferred embodiment, the second attachment means comprises a pair of rigid tabs passing through the sides of the shoe base and secured to the underside of the sole plate. This provides a three-point mounting structure which both holds the vertical uprights tightly against the sides of the base and, by being attached inwardly of the sides and fixed to the sole plate, provides an exceptionally high degree of resistance to torsionally applied forces tending to rotate the upright braces relative to the shoe portion.

In a separate preferred embodiment, the present invention also provides an air cushion for the heel portion of the shoe base to absorb impactive forces when the patient is walking. As the heel hits the ground, the air cushion serves to absorb the impactive forces and reduce the effect of such impacts on the ankle area of the patient's leg. Preferably, the ankle brace comprises a shoe base for releasable attachment to the foot of a patient, the base including lateral sides, a bottom, a toe end, and a heel end, the ankle brace further comprising leg support means, rigidly attached to the base and adapted to be strapped to the leg of a patient above the patient's ankle, the air cushion arrangement being formed in the heel end of the base for absorbing impactive forces when the heel end contacts the ground surface as the patient walks. The air cushion arrangement provides the additional function of maintaining the heel part of the shoe vertically aligned with the shoe sole by resisting sheer forces between these two elements as the patient walks.

Toward this end, the base may comprise an upper base main body and a bottom sole with a heel block. The heel block is somewhat vertically movable relative to the main body due to the compression of the heel block under the weight and impactial forces applied by the patient. Preferably, the heel block or the entire bottom sole is made of soft or medium polyurethane, elastomeric plastic or rubber. The main body has a heel recess therein for receiving the sole plate heel block, and at least one cylindrical piston member projects downwardly from a surface of the recess. The heel block has at least one cylindrical opening therein for receiving the piston in an airtight relationship. As the patient walks and the heel hits the ground, the piston member is forced into the airtight cylinder, and the air compressed within the space between the cylinder and the cylindrical opening absorbs the impactive forces. If desired, the cylindrical piston members can be made hollow so as to enlarge the volume of air being compressed and thereby soften the impactive forces even more as the cylinder is pressed into the cylindrical opening. From a practical viewpoint, and for additional comfort, it is preferred that three such piston/cylinder arrangements be situated in the shoe base and heel block, distributed laterally of the patient's foot. If desired the location of the pistons and cylinders can be interchanged, i.e. the pistons could be formed on the bottom sole, and the heel of the shoe base could be bored to define the cylinders.

In another embodiment of the invention, an ankle brace is provided comprising a shoe base for releasable attachment to the foot of a patient, the shoe base including a bottom, lateral sides, a sole support, a toe end, and a heel end. Removable elongated leg support means can be rigidly attached to the shoe base and adapted to be attached to the leg of a patient above the patient's ankle. Attachment means are provided for attaching the leg support means to the base, such attachment means including first securing means for securing the leg support means to one side of the shoe base, and second securing means for securing the leg support means against rotation of the leg support means about the first securing means.

In another embodiment, the invention relates to a shoe base for use in an ankle brace for releasable attachment to the foot of a patient, the shoe base comprising a monolithic molded main body being formed with lateral sides, a toe end, a heel end, a smooth sole support on its top surface between the sides, and a plurality of open adjacent cellular cavities beneath the sole support, such cavities having closed walls on their tops and sides and being open at their lower extremities.

In another embodiment of the invention, an ankle brace is provided comprising a base for releasable attachment to the foot of a patient, the base including lateral sides, a bottom, a toe end, and a heel end, and further comprising leg support means rigidly attached to the shoe base and adapted to be strapped to the leg of a patient above the patients's ankle, wherein the base comprises an upper main body and a bottom sole, the upper main body being formed with a smooth sole support on its top surface and a box-like undersurface defining a plurality of open adjacent cellular cavities having closed walls on their tops and sides and open at their lower extremities. The bottom sole is adapted to fit over and close off the open cavities. This construction permits lighter weight in the structure of the shoe base and yet requires only a single complex main body portion, thereby reducing costs and minimizing logistics problems in maintaining a supply of different sizes of ankle braces. If desired, an intermediate sole may be provided, which is perfectly alignable with, and firmly affixed to, the main shoe body and attached to the bottom sole by adhesion. This permits a simple construction of the bottom sole itself which may, desirably, be available in many different sizes, styles, and configurations.

BRIEF DESCRIPTION OF THE DRAWINGS

The invention will now be described in more detail, having reference to the attached drawings in which:

FIG. 1 is left elevational view of the ankle brace attached to the foot and lower leg portion of a patient, some of the internal features of the shoe base being shown in phantom lines;

FIG. 2 is a perspective view of the main body of the shoe base with a view from the underside to expose the cellular structure and other important features of the invention;

FIG. 3 is an exploded view of the components making up the shoe base portion of the invention; and FIG. 4 is a perspective view of one of the vertical upright braces which is attachable to the base portion of FIG. 3 and is also attachable to the leg of a patient as shown in FIG. 1.

DETAILED DESCRIPTION OF THE PREFERRED EMBODIMENTS

Referring to FIG. 1, an ankle brace, generally indicated by the numeral 1, is shown to comprise two basic components, a shoe base 3 and a vertical upright brace 5, the combination making up the ankle brace and attached to the patient's leg 7 by means of leg straps 9 and foot straps 11, the attachment to the patient's leg being made by known means of attachment.

The vertical brace 5 is preferably a one-piece molded plastic design having an upwardly extending brace member portion 21 and a lower brace plate portion 23.

The perspective view of FIG. 2 shows the general construction of the upper base main body portion 4 of the shoe base 3. Main body 4 is made of a single-piece casting or molded material such as high-strength lightweight aluminum alloy, magnesium alloy, or engineering plastic, and has a top sole support 43 (shown in FIG. 3), and a cellular structure beneath the sole support 43. The design also includes a heel portion 2, a toe portion 6, and sidewalls 18. In order to maintain high strength and yet have minimum weight, a number of cellular cavities 8 are formed in the bottom of the main body 4, and holes 10 are provided between cavities 8 for purposes of attaching a bottom sole as will be discussed later. This design accomplishes two objectives. It provides a smooth support for the wearer's foot, as opposed to the ribbed support of the prior art, and it locates the part of the shoe base which absorbs shear or torque forces vertically spaced from the shoe base bottom.

At the heel portion 2, the main body 4 is provided with a large heel recess 16 having a horizontal surface 17 from which cylindrical members 12 project. A hole 14 is preferably provided in each cylindrical member 12.

With reference to FIG. 3, an exploded view of the assembly for the shoe base 3 can be seen. As will be readily evident, the main part of the shoe base 3 (FIG. 1) is main body 4 which can be, as previously noted, of monolithic or single-piece construction.

Straps 11 can be mounted to the sidewalls 18 by means of rivets 44 fastened in buckle or strap mounting holes 45. Strap 11 can have coordinating Velcro ® regions which secure the straps together across the user's foot in a manner well known in the industry, and details need not be discussed here.

An aperture 47 is formed in the side of the main body 4 to accept a fastener which holds the vertical brace 5 (FIG. 1) tightly against the side of the main body 4. Passageways 49, 51 may be provided to accommodate a pair of rigid tabs from the vertical brace 5 (to be discussed later). The tabs which are to be inserted in passageways 49 and 51 are secured to the bottom of sole support 43 by means of fasteners such as rivets 55 passing through the tabs of the vertical brace 5 and through corresponding sole apertures 53.

It has been found that an alternative arrangement for securely mounting the brace members 21 to the sides of the shoe base main body 4 is to provide a recess 22 in each side 18, each recess having a flat vertical interior wall 24 and front and rear vertical edges, 25 and 26, respectively. In this embodiment, tabs attached to the sole support 43 are not needed.

A side protector 59 is molded in as part of the unitary construction of the main body 4 so as to aid in protecting the foot from laterally applied impacts to the shoe base 3.

As seen in FIG. 2, one wall of one of the cellular cavities is flush with the planar interior wall surface 24 of recess 22. This design gives added contact area between sidewalls 18 and brace plates 23 and extends the contact area down to the bottom sole level for improved support.

Although aperture 47 may be internally threaded to accommodate screw 27, a more secure arrangement is to provide a nut 36 (FIG. 1) on the end of screw 27, which nut is contained within cellular cavities 37 or 38 (FIG. 2). Alternatively, nut 36 can be molded into the shoe base when it is manufactured.

The bottom sole 71 has upwardly directed studs 63 distributed thereabout on its upper surface, serving two functions. First, the studs 63 serve as locators for perfectly aligning the bottom sole 71 relative to the base main body 4 by the registration of studs 63 with the holes 10 (FIG. 2) provided in the bottom of the main body 4. Additionally, the surface contacting portion 75 of bottom sole 71 serves to distribute the load evenly, aiding in the comfort of the patient.

The heel block 73 of the bottom sole 71 has a number of cylindrical openings 77 which match in position and size the arrangement of cylindrical piston members 12 in heel recess 16 to form a number of cylinder/piston pairs. Since the heel block 73 is somewhat compressible, being made of either a soft or medium soft plastic or rubber material, the cylinder/piston arrangement offers the opportunity of establishing an air cushion effect between the main body 4 and the bottom sole 71. That is, cylindrical piston members 12 are sized to fit snugly into the cylindrical openings 77 so as to form an airtight chamber 19 (FIG. 1). As seen in FIG. 1, the lower extremity of cylindrical piston members 12 are spaced from the bottom 78 of cylindrical opening 77. As a result, when the patient's heel hits the ground, the piston member 12 tends to be pushed further into cylindrical opening 77 and compresses the air beneath the piston. From known pneumatic and mechanical analysis, it can be a appreciated that a degree of shock absorption is experienced by the user through the compression of the trapped air between the piston and the cylinder elements. In order to increase the amount of air trapped between the cylinder and piston, a hole 14 can be made in the center of each piston member 12 so that upon effecting the compression stroke, a larger volume of air is compressed and the amount of impact is correspondingly reduced.

In addition to the air cushion effect, the piston/cylinder arrangement offers a secondary benefit. The cylinder members 12 and cylinder holes 77 are aligned vertically. The large engaging surfaces of these cooperating members prevent deleterious effects due to laterally directed sheer forces between main body 4 and bottom sole 71, unlike the prior art where the component parts of the shoe are glued together. With prior art ankle braces, in time the heels begin to slip sideways, twisting the heel out of position or off the shoe entirely and causing improper healing of the ankle and pain and discomfort to the patient.

In FIG. 4, a perspective view of the vertical brace 5 is depicted. It is of unitary construction and is comprised of a brace plate portion 23 supporting a vertical upright brace member portion 21 which is shown in FIG. 4 as a flat bar having a continually reduced thickness.

The lateral sides of brace plate 23 have vertical end walls 28, 34 which, when vertical brace 5 is in position, adjoin the vertical edges 25, 26 of the shoe brace 3. Screw 27 passes through the lower extremity of vertical brace 5 and into aperture 47. Accordingly, screw 27 holds the vertical brace 5 firmly against the sidewall 18, and brace 5 is thus not permitted to rotate in the plane of brace plate 23 due to the engagement of the vertical edges 25, 26 and end walls 28, 34. Such construction permits easy assembly, a small number of parts, and yet provides a strong and rigid engagement of the brace 5 onto the side of shoe base 3.

To assist in the ability of the shoe base 3 to resist twisting torques applied to brace 3 along the axis of the latter, the recess 22 has a large area planar surface 24 which faces and contacts over the entirety of the corresponding planar portion of the inside surface 35 of brace plate 23.

It will be understood that the recess 22 and cooperating elements of the brace plate 23 are merely one example of a means for resisting twisting torques and rotational torques from twisting or rotation, respectively, of the vertical brace 5 relative to the shoe base 3. For example, a substantial vertically oriented rib (not shown) could project from each side of shoe base 3 and be received in a mating slot in the inner surface of brace plate 23. It is sufficient, for the purposes of this invention, however, to provide some means of locking the vertical brace 5 into position against such twisting or rotating forces by the interaction of cooperating vertical members between the shoe base 3 and the brace plate 23. In this way, a simple, single, attachment screw 27 is all that is necessary to assemble and result in a very rigid and torque resistant assembly.

FIG. 4 shows optional tabs 29 projecting inwardly from the inward surface of brace plate 23. In the embodiment described in the previous paragraph, the integrity of the structure is intact without any additional support. However, in some instances it may be desirable to have even additional resistance to rotational forces applied against brace 5 tending to rotate the brace about screw 27. In such an environment, tabs 29 may be useful. It is to be understood, however, that such tabs 29 are indeed optional.

Projecting inwardly from the brace plate 23 are the pair of optional rigid tabs 29, each with holes 33 adjacent their extremities. A hole 31 may also be provided to add additional mounting strength to the unit and assist in resisting torsional forces exerted between the vertical brace 5 and the shoe base 3, the hole 31 aligned with hole 32 (FIG. 3) in sidewall 18 of the main body 4. Rigid tabs 29 are preferably cast or molded integrally with brace plate 23. Brace member 21 may also be cast or molded along with brace plate 23, or the two units can be manufactured separately and connected together by known means.

A fastener 27, for example a threaded screw, having an axis substantially perpendicular to one side of the shoe base, projects through the bottom of the brace plate 23 and screws into, or is fastened to, the sidewall 18 through aperture 47 shown in FIG. 3. The connection made by fastener 27 serves to hold the vertical brace 5 tightly against the sidewall 18 of the shoe base 3 in manner similar to that which is already known in the art. However, as explained earlier, due to the lack of substantial resistance to torque being applied to the mounting means connecting a vertical brace to a shoe base according to the prior art, additional torque resistance is realized according to the present invention by the provision of the recess 22 and the rather large rigid projecting tabs 29, 30 which fit, respectively, into passageways 51 and 49 of main body 4 (FIG. 3) and secured inwardly of the side of the shoe base and laterally of the axis of the fastener 27. The free ends of tabs 29 are arranged to fit tightly against the undersurface of sole support 43.

While the arrangement showing FIGS. 3 and 4 are of a particular design, it is to be understood that other arrangements of tabs and/or openings in the sidewall 18 can be made without departing from the concept of substantially increasing the resistance to torque applied to the vertical brace 5. For example, sidewall 18 of main body 4 can have an opening which spans the side of the shoe base 3 from adjacent the heel portion to adjacent the rear of side protector 59. In this manner, the free ends of tabs 29, 30 can be easily positioned to lie flat against the undersurface of sole plate 43 and held in place by rivets 55 passing through holes 33 in the ends of tabs 29, 30 and through the holes 53 in the sole support 43. In any case, with or without the sidewall 18 extending completely longitudinally of the side of the main body 4, fastener 27 can secure the vertical brace 5 to the side of the shoe base 3 by a fastening connection to a wall of one of the cellular cavities 8 provided with a mounting hole 20 as shown in FIG. 2.

I claim:
1. An ankle brace comprising:
a shoe base for releasable attachment to the foot of a patient, said shoe base including a bottom, lateral sides each having an inner surface and an outer surface, a sole support, a toe end, and a heel end;
removable elongated leg support means for rigid attachment to said shoe base and adapted to be attached to the leg of a patient above the patient's ankle; and
attachment means for attaching said leg support means to said shoe base, said attachment means including first securing means for securing said leg support means to the outer surface of one lateral side of said shoe base, and second securing means for securing said leg support means against rotation and against twisting of said leg support means relative to said shoe base; wherein:
said first securing means comprises a fastener passing, perpendicular to said outer surface, through a first aperture in said leg support means and fixed to said shoe base; and
said second securing means comprising cooperating vertical wall means on said leg support means and on said one lateral side of said shoe base, said coop- erative vertical wall means engaging one another to thereby resist any rotation about said fastener of said leg support means relative to said lateral side of said shoe base.

2. The ankle brace as claimed in claim 1, wherein said cooperating vertical wall means comprises:
a vertical recess in said outer surface of said one lateral side of said shoe base, the side edges of which define front and rear recess edges; and
vertical sidewalls on the lower lateral sides of said leg support means; whereby
when said leg support means is secured to said one lateral side of said shoe base by said first securing means, said vertical sidewalls of said leg support means engage said front and rear recess edges.

3. The ankle brace as claimed in claim 2, wherein:
said vertical recess has a flat interior supporting surface extending between said front and rear recess edges; and
said leg support means has a flat engaging surface extending between said vertical sidewalls; whereby
when said leg support means is secured to said one lateral side of said shoe base by said first securing means, said flat supporting surface and said flat engaging surface are coplanar and engaging one another, thereby resisting twisting of said leg support means about the longitudinal vertical axis of said leg support means.

4. The ankle brace as claimed in claim 3, wherein:
said leg support means has an upper end and a lower end; and
said second securing means comprises a tab extending from said leg support lower end substantially perpendicular to said leg support flat engaging surface, said tab having a free end passing under said sole support.

5. An ankle brace as claimed in claim 1, wherein said second securing means comprises means for securing said leg support means to the underside of said sole support inwardly of said inner surface of said one lateral side and laterally of a line perpendicular to said one lateral side at the position of said first securing means.

6. The ankle brace as claimed in claim 1, wherein said leg support means comprises:
a brace plate portion for attachment to said shoe base; and
an elongated vertical brace member extending upwardly from said brace plate portion, the thickness of said brace member diminishing toward its upper end.

7. The ankle brace as claimed in claim 1, wherein said shoe base is a molded plastic member, and said sole support is formed as a continuous surface extending between said lateral sides and between said toe and heel ends, and is spaced from said shoe base bottom by downwardly extending ribs defining a plurality of open ended cells, said cells being closed against said sole support and opening toward said shoe base bottom.

8. An ankle brace comprising :
a shoe base for releasable attachment to the foot of a patient, said shoe base including a bottom, lateral sides each having an inner surface and an outer surface, a sole support, a toe end, and a heel end;
leg support means for rigid attachment to said shoe base and adapted to be attached to the leg of a patient above the patient's ankle; and
attachment means for attaching said leg support means to said shoe base, said attachment means including firs securing means for securing said leg support means to the outer surface of one lateral side of said shoe base, and second securing means for securing said leg support means to the underside of said sole support inwardly of said inner surface of said one lateral side and laterally of a line perpendicular to said one lateral side at the position of said first securing means.

9. The ankle brace as claimed in claim 8, wherein:
said leg support means has an upper end and a lower end;
said first securing means comprises a fastener passing, perpendicular to said outer leg support means outer surface, through a first aperture in said leg support means and fixed to said shoe base; and
said second securing means comprises a tab extending from said leg support lower end and substantially perpendicular to said one lateral side, said tab having a free end passing under said sole support and fixed to the underside of said sole support.

10. The ankle brace as claimed in claim 9, wherein said second securing means comprises a second tab having a free end passing under said sole support and fixed to the underside of said sole support, said second tab spaced from said first-mentioned tab, with said first securing means disposed between said first and second tabs.

11. The ankle brace as claimed in claim 10, wherein:
said leg support means comprises a pair of vertical brace members attached to respective outer surfaces of said lateral sides of said shoe base;
said lateral sides of said shoe base have passageways therein for receiving said tabs; and
said second securing means comprises fasteners passing through apertures in said tabs and fixed to said sole plate.

12. An ankle brace comprising:
a shoe base for releasable attachment to the foot of a patient, said shoe base including lateral sides, a bottom, a sole support, a toe end, and a heel end;
leg support means rigidly attached to said shoe base and adapted to be attached to the leg of a patient above the patient's ankle; and
an air cushion arrangement in said heel end of said shoe base for absorbing impactive forces when said heel end contacts a ground surface as the patient walks; wherein:
said shoe base comprises an upper shoe base main body and a bottom sole with a heel block;
said heel block is vertically movable relative to said main body;
said main body has a heel recess therein for receiving said heel block and includes at least one cylindrical piston member projecting downwardly from a surface of said recess; and
said heel block has at least one cylindrical opening therein for receiving said piston member in an airtight relationship.

13. The ankle brace as claimed in claim 12, wherein said cylindrical piston member is hollow to provide a compressed air trap when said piston member is moved into said cylindrical opening.

14. The ankle brace as claimed in claim 12, wherein the number of cylindrical piston members and the number of complementary cylindrical openings is three, said piston members and cylindrical openings being arranged uniformly in said heel end of said shoe base.

15. The ankle brace as claimed in claim 12, wherein:
   said bottom sole has a plurality of studs projecting from its upper surface; and
   said main body has a plurality of apertures formed in its bottom surface; whereby
   when assembled, said bottom sole studs fit snugly into said main body bottom surface apertures, for easy location of said bottom sole relative to said main body, and for quickly attaching said bottom sole to said main body.

16. The ankle brace as claimed in claim 12, wherein said shoe base comprises:
   an upper sole base main body; and
   a bottom sole with at least one cylindrical piston member projecting upwardly from the heel end of said bottom sole, wherein:
   said heel block is vertically movable relative to said main body; and
   said main body has at least one cylindrical opening at its heel end for receiving said piston member in an airtight relationship.

17. The ankle brace as claimed in claim 12, wherein said shoe base comprises an upper main body and a bottom sole, said upper main body being formed with a smooth sole support on its top surface and a plurality of open adjacent cellular cavities on its bottom, said cavities having closed walls on their tops and sides and being open at their lower extremities, said bottom sole adapted to fit over and close off said open cavities.

* * * * *